(12) United States Patent
Haselton

(10) Patent No.: US 9,677,979 B2
(45) Date of Patent: Jun. 13, 2017

(54) LOW RESOURCE PROCESSOR USING SURFACE TENSION VALVES FOR EXTRACTING, CONCENTRATING AND DETECTING MOLECULAR SPECIES

(75) Inventor: Rick Haselton, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 662 days.

(21) Appl. No.: 13/809,722

(22) PCT Filed: Jul. 15, 2011

(86) PCT No.: PCT/US2011/044167
§ 371 (c)(1),
(2), (4) Date: Mar. 18, 2013

(87) PCT Pub. No.: WO2012/009627
PCT Pub. Date: Jan. 19, 2012

(65) Prior Publication Data
US 2013/0183678 A1    Jul. 18, 2013

Related U.S. Application Data

(60) Provisional application No. 61/365,170, filed on Jul. 16, 2010.

(51) Int. Cl.
*C12Q 1/68* (2006.01)
*G01N 1/34* (2006.01)
*B01L 3/00* (2006.01)
*G01N 33/543* (2006.01)

(52) U.S. Cl.
CPC .......... *G01N 1/34* (2013.01); *B01L 3/502738* (2013.01); *B01L 3/502784* (2013.01); *C12Q 1/6806* (2013.01); *G01N 33/54326* (2013.01); *B01L 2200/0647* (2013.01); *B01L 2300/0838* (2013.01); *B01L 2300/0883* (2013.01); *B01L 2400/043* (2013.01); *B01L 2400/0688* (2013.01)

(58) Field of Classification Search
None
See application file for complete search history.

(56) References Cited

U.S. PATENT DOCUMENTS

| | | | | |
|---|---|---|---|---|
| 6,743,399 B1 * | 6/2004 | Weigl et al. | .................. | 422/504 |
| 7,309,439 B2 * | 12/2007 | Fernandez et al. | ........... | 210/695 |
| 7,445,754 B2 * | 11/2008 | Chung et al. | ................ | 422/505 |

(Continued)

FOREIGN PATENT DOCUMENTS

| | | |
|---|---|---|
| WO | WO 2009/044088 | 4/2009 |
| WO | WO 2009/111316 | 9/2009 |
| WO | WO 2010/077859 | 7/2010 |

OTHER PUBLICATIONS

Berry et al. (Lab On a Chip, 2011, vol. 11, p. 1747).*

(Continued)

*Primary Examiner* — Stephanie K Mummert
(74) *Attorney, Agent, or Firm* — Parker Highlander PLLC

(57) ABSTRACT

Systems and methods are described for isolation, separation and detection of a molecular species using a low resource device for processing of samples. Methods include isolation, separation and detection of a molecular species for protein-protein, DNA-DNA and other chemical interactions.

37 Claims, 12 Drawing Sheets

(56) References Cited

U.S. PATENT DOCUMENTS

| | | | |
|---|---|---|---|
| 7,521,261 B2* | 4/2009 | Haselton | C40B 30/04 436/518 |
| 2005/0053952 A1* | 3/2005 | Hong | B01L 3/50273 435/6.14 |
| 2006/0003439 A1 | 1/2006 | Ismagilov et al. | |

OTHER PUBLICATIONS

MagMax™ Magnetic Particles, Life Technologies, 2015, p. 1-3.*
Office Action issued in Chinese Application No. 201180044832.8, dated Jun. 10, 2014.
Chen et al., "An integrated, self-contained microfluidic cassette for isolation, amplification, and detection of nucleic acids", *Biomed. Microdevices*, 12(4):705-719, 2010.
Hagan et al., "An integrated, valveless system for microfluidic purification and reverse transcription-PCR amplification of RNA for detection of infectious agents", *Lab. Chip.*, 11(5):957-61, 2011.
Niemz et al., "Point-of-care nucleic acid testing for infectious diseases", *Trends Biotechnol.*, 29(5):240-250, 2011.
PCT International Preliminary Report on Patentability issued in International Application No. PCT/US2011/044167, mailed Jan. 31, 2013.
PCT International Search Report and Written Opinion issued in International Application No. PCT/US2011/044167, mailed Jan. 11, 2012.
Price et al., "Nucleic acid extraction techniques and application to the microchip", *Lab. Chip.*, 9(17):2484-2494, 2009.

* cited by examiner

LOW RESOURCE PROCESSOR USING SURFACE TENSION VALVES FOR EXTRACTING, CONCENTRATING AND DETECTING MOLECULAR SPECIES

CROSS-REFERENCE TO RELATED APPLICATION

This application is a national phase application under 35 U.S.C. 371 of International Patent Application No. PCT/US2011/044167, filed Jul. 15, 2011, which claims priority to U.S. Provisional Patent Application Ser. No. 61/365,170 filed Jul. 16, 2010, each of which is herein incorporated by reference in its entirety.

BACKGROUND OF THE INVENTION

1. Field of the Invention

The invention relates generally to the field of diagnostics and detection. More particularly, the invention relates to low resource processors for assessing molecular interactions. Specifically, the invention relates to the use of devices containing multiple chambers separated by surface tension valves for the processing of microbeads having screening reagents attached thereto. The device permits assaying for the content of a wide variety of environmental and biological samples. In addition, specific interactions such as DNA-DNA interactions, DNA-protein interactions, or protein-protein interactions, ion-protein interactions, enzyme-substrate interactions can be assessed.

2. Discussion of the Related Art

Recent research has focused on the development of nucleic acid-based detection for low resource settings (Niemz et al., 2011). Nucleic acid-based detection systems, such as quantitative PCR (qPCR), are particularly attractive technologies for detection of pathogens because of their sensitivity, specificity and relatively rapid time-to-answer. The effectiveness of PCR is dependent on both the quality and quantity of nucleic acid template (Beuselinck et al., 2005) and the absence of interferents (Radstrom et al., 2004). For example, carbohydrates, proteins, lipids or other unidentified interferents present in clinical samples have all been shown to inhibit PCR and produce false negatives (Monteiro et al., 1997; Wilson, 1997; Coiras et al., 2003). In addition to various interferents, patient samples also contain nucleases, which directly reduce the number of nucleic acid targets present (Wilson, 1997).

To minimize false negatives and maximize the efficiency of nucleic acid-based diagnostics, nucleic acids are extracted and concentrated into an interferent-free buffer prior to testing. One classic laboratory method uses a phenol-chloroform cocktail (Chomczynski and Sacchi, 1987). This method is highly effective, but is not as commonly utilized today because it is time consuming and requires the use of toxic organic chemicals. Several solid phase extraction kits are commercially available to purify DNA or RNA from patient samples. Many of these kits rely on selective nucleic acid binding to silica-coated surfaces in the presence of ethanol and a chaotropic agent such as guanidinium thiocyanate (GuSCN) (Avison, 2007; Yamada et al., 1990). GuSCN also denatures protein contaminants including nucleases that may be present in the sample (Chirgwin et al., 1979; MacDonald et al., 1987). These kits are not cost effective for low resource use and often require the use of specialized laboratory equipment, such as a robot or centrifuge, and trained technicians that are unavailable in a low resource setting. Additionally, many involve multiple steps that increase the chance of contamination of both the sample and operator.

Microfluidics is one promising format for low resource nucleic acid-based diagnostics. Recently, there has been a growing interest in expanding microfluidic technologies for sample preparation (Niemz et al., 2011; Price et al., 2009). Many of these devices are suitable for integrating with downstream nucleic acid amplification and detection technologies (Chen et al., 2010; Hagan et al., 2011). However, the small surface area of solid phase available for nucleic acid binding and the limited sample volume that can be flowed through the channels limit the total mass of nucleic acid recovered (Niemz et al., 2011), and therefore negatively impact the limit of detection.

For example, the analysis of transrenal DNA for diagnosis of TB is an attractive alternative to traditional diagnostic methods such as sputum microscopy, especially as nucleic acid-based technologies become increasingly more relevant in low resource settings (Huggett et al., 2009). PCR analysis of patient urine samples is ineffective for some of the same reasons noted above. It is thought that one of the principle reasons is the high variation in salts contained in urine samples. However, the collection of urine is thoroughly noninvasive. This is particularly advantageous in high disease burden settings where limited resources and lack of skilled technicians may make sample collection difficult (Umansky and Tomei, 2006; Green et al., 2009). Additionally, the collection of urine provides a much larger sample volume than other more invasive methods such as sputum collection. While transrenal DNA is present in relatively low concentrations (~6 to 50 ng/mL in healthy subjects (Bryzgunova et al., 2006)), the ability to collect and test a large volume ensures that there is sufficient material available to make an accurate diagnosis. Finally, the analysis of purified transrenal DNA can be multiplexed to detect the presence multiple pathogens simultaneously. For example, coinfection of TB with HIV is a common problem in Sub-Saharan Africa (Green et al., 2009). A multiplex detection assay designed to diagnose both TB and HIV would be ideal this setting.

The concept of transrenal DNA analysis for the diagnosis of tuberculosis is emerging as an attractive alternative to traditional diagnostic methods, particularly as nucleic acid-based technologies become increasingly more relevant in low resource settings. As dying human cells and microorganisms are broken down, small nucleic acid fragments can end up in the blood stream, and subsequently pass through the kidneys and into the urine (Botezatu et al., 2000). The analysis of transrenal DNA fragments for mycobacterial DNA has been demonstrated to be a promising technique for the diagnosis of tuberculosis and offers several advantages over traditional sputum microscopy (Aceti et al., 1999; Cannas et al., 2008; Gopinath and Singh, 2009). The collection of urine is thoroughly noninvasive. This is particularly advantageous in high disease burden settings where limited resources and lack of skilled technicians may make sample collection difficult (Umansky and Tomei, 2006; Green et al., 2009). Additionally, the collection of urine provides a much larger sample volume than sputum collection. While transrenal DNA is present in relatively low concentrations (~6 to 50 ng/mL in healthy subjects (Bryzgunova et al., 2006)), the ability to collect and test a large volume ensures that there is sufficient material available to make an accurate diagnosis. Finally, the analysis of mycobacterium-specific DNA sequences is inherently more sensitive than microscopic diagnosis (Huggett et al., 2009).

In the absence of appropriate methodologies, sputum microscopy remains the current worldwide standard for the diagnosis of tuberculosis. Unfortunately, the collection of sputum samples can potentially produce infectious aerosols, which is particularly problematic in low resource settings where trained personnel are frequently unavailable (Cannas et al., 2008). Microscopic diagnosis is time consuming and suffers from limited sensitivity (Green et al., 2009). However, because methods for purifying DNA from urine in low resource environments prior to any nucleic acid-based diagnostic test are not available, this remains the preferred approach.

Similar issues relate to the testing for other molecular species including proteins, lipids and carbodyrates. In general, detection of any molecular species of interest is made much more difficult by the presence of interferents contained in a "real" sample. Therefore, a rapid, noninvasive diagnostic technology is desirable, especially in low resource environments.

SUMMARY OF THE INVENTION

Thus, in accordance with the present invention, there is provided a method of processing a sample comprising (a) providing a device comprising a plurality of sequential chambers each comprising a fluid and separated by surface tension valves, wherein a first reaction chamber comprises a particle having a reactant on its surface; (b) introducing into said first reaction chamber a sample; (c) incubating said first reaction chamber under conditions sufficient to permit reaction of said reactant with an analyte in said sample; (d) transporting said particle from said first reaction chamber into at least a second chamber; and (e) detecting interaction of said analyte with said reactant. Other chambers include an elution chamber and/or a concentration chamber. The device may comprise at least three chambers, such as a first reaction chamber, a first processing chamber and a first detection chamber, wherein said first processing chamber is disposed between said first reaction chamber and said first action chamber. The method may also further comprise reversing the transport of said particle to reintroduce said particle into a chamber through which it has already passed. In some embodiments, the target molecular species are separated from the beads in the final chamber. These targets are then further analyzed such as a RT-PCR or PCR reaction.

The device may comprise continuous tubing and surface tension valves separating said tubing into said plurality of chambers. The tubing may be made of glass, a polymer or a metal. The tubing may comprise an inner surface coated by a polymer. The particle may be a magnetic particle, a paramagnetic particle or a non-magnetic particle having a density of different than the surrounding fluid. Transporting may comprise passing a magnetic field along said tubing or subjecting said tubing to distinct intermittent magnetic fields to effect movement of said particle. Transporting may instead comprise applying centrifugal force to said device such that said particle is transported through said plurality of chambers. Alternatively, one can perform processing using gravitational settling with a high density bead (optionally magnetic) contained in a lower density fluid, or buoyancy forces that arise from a low density particle contained within a higher density liquid.

The analyte may be a protein, a polypeptide, a lipid, a carbohydrate, a nucleic acid, a heavy metal, an organochemical compound, a bacterium, a virus, or a fungal cell. protein an antigen, an antibody, or an enzyme. The reactant may be an antibody, an antigen, a chelating agent, a lipid, a carbohydrate, a metal, an organochemical compound, an enzyme substrate, or a nucleic acid. Detecting the interaction of said analyte with said reactant may comprise FRET, colorimetric assay, fluorescence assay, RT-PCR, change in optical density, or change in refractive index. Introducing may comprise injecting said sample through a wall of said first reaction chamber. To facilitate introduction, the wall of said first reaction chamber may comprise a port facilitating injection of said sample. Samples can also load by "capillary" action, meaning transfer of fluid into a bundle of small diameter capillary tubes.

The sample may be a biological sample, such as a tissue or fluid sample obtained from a patient. The sample may be an environmental sample such as a soil sample, a water sample, or a plant sample. The particle may be 0.1 to 10 micrometers in diameter, and the tubing may be 0.5 to $10^4$ micrometers inner diameter. The surface tension valve may comprise a non-reactive gas or a fluid having low vapor pressure or low surface tension, such as a non-reactive gas like air, carbon dioxide, nitrogen, argon, helium, or sulfur hexafluoride, or a fluid like mineral oil, Dodecane, 1-Dodecene, Tridecane, Methyloleate, Acetophenone, Propyl Benzoate, or 1-Methylnaphthalene.

Another embodiment comprises a device comprising a plurality of sequential chambers each comprising a fluid and separated by surface tension valves. The device may comprise at least three chambers, such as a first reaction chamber, a first processing chamber and a first detection chamber, wherein said first processing chamber is disposed between said first reaction chamber and said first action chamber. Other chambers include an elution chamber and/or a concentration chamber. The device may comprise continuous tubing and surface tension valves separating said tubing into said plurality of chambers. The tubing may be made of glass, a polymer or a metal, and the tubing may be 0.5 to $10^4$ micrometers in diameter. The tubing may comprise an inner surface coated by a polymer. The surface tension valve may comprise a non-reactive gas or a fluid having low vapor pressure or low surface tension, such as a non-reactive gas like air, carbon dioxide, nitrogen, argon, helium, or sulfur hexafluoride, or a fluid like mineral oil, Dodecane, 1-Dodecene, Tridecane, Methyloleate, Acetophenone, Propyl Benzoate, or 1-Methylnaphthalene. The device may also comprise a particle comprising a surface reactant. The device may also comprise a magnetic field source.

In yet another embodiment, there is provided a method of processing a sample comprising (a) providing a device comprising a plurality of sequential chambers each comprising a fluid and separated by surface tension valves; (b) introducing into said first chamber a particle comprising a surface reactant, the surface of which comprises analyte bound to said reactant; (c) transporting said particle from said first chamber into at least a second chamber; and (d) detecting the presence of said analyte. The method may further comprise mixing said particle with a sample to permit binding of said analyte to said reactant on said particle. The particle may be a magnetic particle, a paramagnetic particle or a non-magnetic particle having a density different than the surrounding fluid. Transporting may comprise passing a magnetic field along said tubing or subjecting said tubing to distinct intermittent magnetic fields to effect movement of said particle. Transporting may instead comprise applying centrifugal force to said device such that said particle is transported through said plurality of chambers, or by density driven transport, e.g., a very dense particle falling through a less dense liquid, or a less dense buoyant particle rising within a more dense liquid.

The analyte may be a protein, a polypeptide, a lipid, a carbohydrate, a nucleic acid, a heavy metal, an organochemical compound, a bacterium, a virus, or a fungal cell. protein an antigen, an antibody, or an enzyme. The reactant may be an antibody, an antigen, a chelating agent, a lipid, a carbohydrate, a metal, an organochemical compound, an enzyme substrate, or a nucleic acid. Detecting the interaction of said analyte with said reactant may comprise FRET, colorimetric assay, fluorescence assay, RT-PCR, change in optical density, or change in refractive index. Introducing may comprise injecting said sample through a wall of said first reaction chamber. To facilitate introduction, the wall of said first reaction chamber may comprise a port facilitating injection of said sample.

The sample may be a biological sample, such as a tissue or fluid sample obtained from a patient. The sample may be an environmental sample such as a soil sample, a water sample, or a plant sample. The particle may be 0.1 to 10 micrometers in diameter, and the tubing may be 0.5 to $10^4$ micrometers inner diameter. The device may comprise at least three chambers, such as a first reaction chamber, a first processing chamber and a first detection chamber, wherein said first processing chamber is disposed between said first reaction chamber and said first action chamber.

The surface tension valve may comprise a non-reactive gas or a fluid having low vapor pressure or low surface tension, such as a non-reactive gas like air, carbon dioxide, nitrogen, argon, helium, or sulfur hexafluoride, or a fluid like mineral oil, Dodecane, 1-Dodecene, Tridecane, Methyloleate, Acetophenone, Propyl Benzoate, or 1-Methylnaphthalene.

Also provided is a kit comprising a device comprising tubing comprising a plurality of sequential chambers each comprising a fluid and separated by surface tension valves. The kit may further comprise particles disposed in at least one of said chambers, or further comprising particles disposed in a distinct container.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The drawings accompanying and forming part of this specification are included to depict certain aspects of the invention. A clearer conception of the invention, and of the components and operation of systems provided with the invention, will become more readily apparent by referring to the exemplary, and therefore non-limiting, embodiments illustrated in the drawings, wherein like reference numerals (if they occur in more than one view) designate the same elements. The invention may be better understood by reference to one or more of these drawings in combination with the description presented herein. It should be noted that the features illustrated in the drawings are not necessarily drawn to scale.

Figure 1:
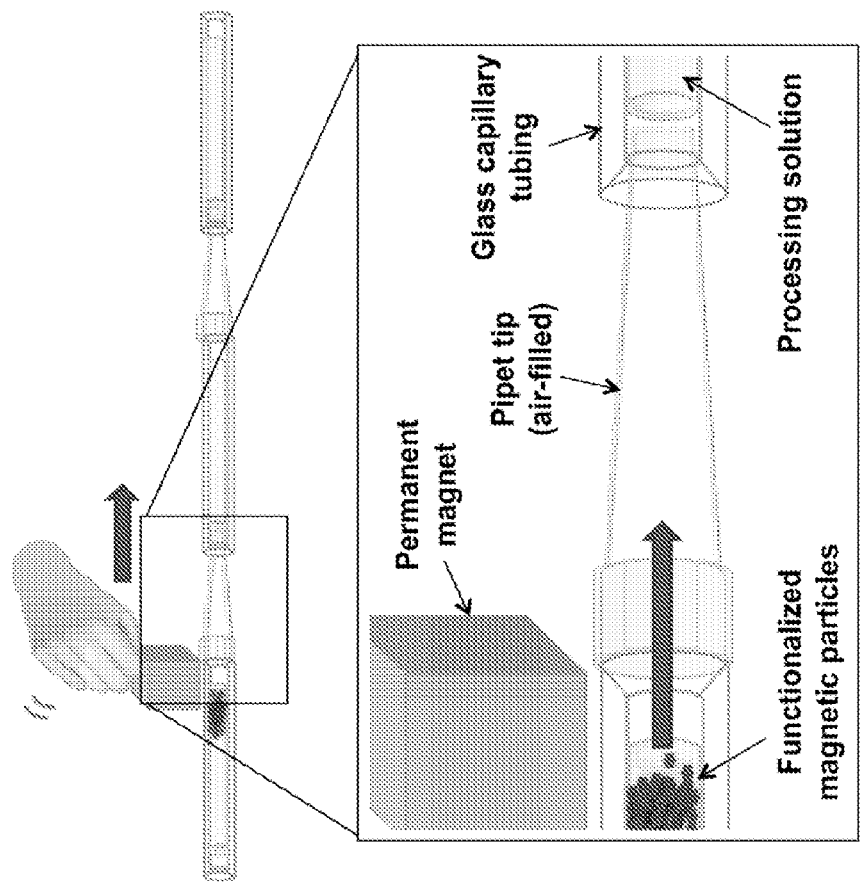
FIG. 1—Design of the prototype extraction method showing three processing solutions held in place in glass tubing and separated by air-filled pipette tips. RNA is adsorbed to silica-coated magnetic particles which are pulled left to right through successive processing chambers using an external magnet. Following processing, the RNA is eluted in a final water chamber.

DESCRIPTION OF PREFERRED
EMBODIMENTS

As discussed above, a major impediment to the use of simple and rapid assays for detecting analytes is the presence of contaminants contained in patient samples that block the effectiveness of such methods. For instance, it has been shown that high concentrations of carbohydrates present in clinical samples can inhibit the results of PCR. In addition to containing contaminants which inhibit nucleic acid-based detection, patient samples also contain DNases and RNases which, over time, reduce the number of nucleic acid targets present in the samples. A number of nucleic acid extraction kits are commercially available for use in a laboratory setting. However, they require laboratory equipment such as centrifuges and pipettes. The overall goal is to develop a self-contained low resource device to extract molecules such as nucleic acids or proteins from samples and concentrate the targets in an elution buffer that can be used in a variety of downstream applications without the need for complicated or expensive methodologies.

The inventors have developed an alternative nucleic acid extraction cassette suitable for operation in a low resource setting. This self-contained extraction cassette is preloaded with processing solutions separated by air gaps, which are referred to as "surface tension valves." In RNA extraction studies, RSV infected cells are lysed and viral RNA is selectively adsorbed to silica-coated magnetic particles in the presence of GuSCN and ethanol. Individual processing solutions are preloaded into a single continuous length of Tygon tubing and are separated from one another and held in places by surface tension forces. Removal of interfering agents is achieved by selective RNA adsorption to silica-coated magnetic particles which are then pulled through each processing solution using an externally applied magnetic field. RNA is eluted from the surface of the magnetic particle in the final solution. This report describes the general characteristics of this approach and compares its performance to laboratory-based commercial kits.

The present invention therefore provide a unique solution to problems relating to low cost biomolecular isolation, separation and detection technology, where reactants are rendered "mobile" by disposing them on particles which can be easily manipulated through various "zones" of an apparatus or system. The different zones separate various solutions, including reaction and processing zones. One important aspect of the invention is the use of surface tension valves to segregate the different zones while permitting the transport of the particles through each zone. Surprisingly, the particles can pass through these air valves despite considerable surface tension, and can do so without transferring liquids from one chamber to another. Thus, the present invention can solve many problems currently limiting the application of biomolecular isolation, separation and detection technologies and create new areas of application as well. These and other aspects of the invention are described in greater detail below.

A. The Device

In general, device will have the following components. First, a continuous tubing will provide the basis for creating a plurality of chambers. The chambers are, in essence, liquid pockets that are maintained separate from each other by the use of surface tension valves, which are fluid or gaseous agents interspersed between the fluid pockets. The device may also include predisposed therein particles for use in detecting analytes that are introduced into the device. Finally, the device may be provided without the liquid pockets, but instead may contain the liquids and fluid/gaseous components in separate containers (i.e., a kit) for use or distribution into/customization of the device at the point of implementation. The individual elements of the device will be discussed in greater detail below.

1. Tubing

Central to the design of this device is the establishment of a series of solutions arrayed along a tube each separated from the next by a surface tension valve. Only tubing of sufficiently small diameter will allow for a stable arrangement of the fluids and valves. Tubing of diameter greater than about 4 mm will not support stable valve formation. Therefore an important physical property of this component is its diameter.

The tubing may be made of a variety different materials including glass, polymers or metal. The tubing should be made of, or internally coated with, a polymer that permits formation of surface tension valves, discussed further below. It is also desirable to have tubing with low surface energy, meaning that it is non-binding for proteins, and also hydrophobic. These properties of the tubing material affect the stability of the arrayed solutions and therefore the diameter of the tubing that is useable. Lower surface energy generally will require a tubing of smaller diameter to permit stable valve formation. Typical surface energy values for glass, silanized glass, polystyrene, Teflon and some types of fluorinated ethylene polypropylene Tygon tubing are in the range of 10-50, 10-30, 15-30, 20-30, 5 mN/m, including 10, 15, 18.5, 20, 25, 30, 35, 40, 45 and 50 mN/m.

A particular type of tubing is Tygon tubing, which is a brand name for a variety of flexible tubing. Tygon is a registered trademark of Saint-Gobain Corporation. Tygon Tubing is used in many markets including food and beverage, chemical processing, industrial, laboratory, medical, pharmaceutical, and semiconductor processing. There are many formulations of clear, flexible, Tygon tubing. The chemical resistance and physical properties vary among the different formulations, but the tubing generally is considered resistant to almost any chemical attack.

Several formulations of Tygon are Class VI approved and can be used in either surgical procedures or pharmaceutical processing. Medical versions include the following:

Tygon Medical/Surgical Tubing S-50-HL—Characterized to the latest ISO 10993 standards and FDA guidelines for biocompatibility. This material is non-toxic, non-hemolytic, and non-pyrogenic. This formulation is used in minimally invasive devices, dialysis equipment, for bypass procedures, and chemotherapy drug delivery.

Tygon Medical Tubing S-54-HL was introduced in 1964 for use in medical applications. This material can be used in catheters, for intravenous or intra-arterial infusion and other surgical uses. Tygon S-54-HL can also be fabricated into cannulae or protective sheath products using thermoforming and flaring techniques.

Pharmaceutical Tygon includes:

Tygon LFL (Long Flex Life) pump tubing is non-toxic clear tubing with broad chemical resistance. It is often used in product filtration and fermentation and surfactant delivery.

Tygon 2275 High Purity Tubing is a plasticizer-free material that is often used in sterile filling and dispensing systems and diagnostic equipment. This formulation is also considered to have low absorption/adsorption properties which minimizes the risk of fluid alteration.

Tygon 2275 I.B. High-Purity Pressure Tubing is plasticizer-free and is reinforced with a braid for use with elevated working pressures.

Tygon chemfluor FEP is a non-protein binding tubing which contains no additives or plasticizers. FEP stands for fluorinated ethylene propylene.

Peristaltic applications include the following:

Tygon R-3603 Laboratory Tubing is commonly used in university laboratories. It is often used in incubators, hoods and as a replacement for rubber tubing for Bunsen burners. This material is produced in vacuum sizes and can withstand a full vacuum at room temperature.

Tygon R-1000 Ultra-Soft Tubing is used in general laboratory applications. It is the softest of the Tygon formulations with a durometer hardness of Shore A 40 (ASTM Method D2240-02). Because of the low durometer of this material it is often used in low-torque peristaltic pumps.

Tygon LFL (Long Flex Life) Pump Tubing, Tygon 3350, Tygon S-50-HL Medical/Surgical Tubing, Tygon 2275 High Purity Tubing, and Tygon 2001 Tubing are also used in peristaltic pump applications.

Other types of tubing include the following. Silicone Tubing (LPS), which is the most commonly used peristaltic pump tubing. It provides the longest service life and good chemical compatibility for aqueous solvents. Silicone tubing can be autoclaved a single time using a wet cycle. Vinyl Tubing (LPV) has the lowest per-foot cost of the available peristaltic pump tubings. It generally has only fair compatibility for most aqueous solvents and does not have a good tolerance for organic solvents. It has only about one-third the service live of silicone tubing in a peristaltic pump. Vinyl tubing should not be autoclaved or exposed to temperatures above 80° C. Fluoroelastomer Tubing (LPF) is both the most chemically inert and the shortest lived peristaltic pump tubing. It can even withstand halogenated solvents for a limited time. Its service life is only about one-twentieth that of silicone tubing in a peristaltic pump. Like silicone tubing, fluoroelastomer tubing can be autoclaved a single time using a wet cycle. Teflon® Tubing (HPT) is the most inert of all the tubing we manufacture. It can withstand nearly any solvent used in a modern laboratory, from distilled water to methylene chloride. Its excellent thermal characteristics allow it to be autoclaved repeatedly. After autoclaving Teflon tubing should not be used for fluid transport until it has cooled. Polyethylene Tubing (HPP) is an inexpensive alternative to Teflon tubing. Like Teflon tubing, polyethylene can handle pressure significantly higher than any of other flexible tubings. Polyethylene does not have the thermal stability of Teflon so it should not be autoclaved; it can, however, be sterilized ethylene oxide.

2. Chambers

The present inventors have designed processing chambers, equipped with gas/fluid valves, that permit the passage of particles into and out of the chambers without substantial loss of liquids, and preservation of each compartment's integrity. In a particular embodiment, the processing chambers are configured to provide down to nanoliter volumes. Reaction, processing, hybridization, and analysis steps can be conducted in a series of separate chambers. In general, the chambers contain aqueous liquids that contain various chemical and biological species, such as salts, dyes, labels and other chemical species. Examples of the disposition of the chambers and their relationship to one another is illustrated in FIGS. 1-4.

Referring to FIG. 1, the user is shown pulling a cube magnet along the sections of tubing joined by plastic pipette tips containing air. The motion of the cube magnet transports magnetic particles across the solution/air interfaces. In the inset, the arrow shows the beads entering the air separating the two liquid solutions.

Figure 2:
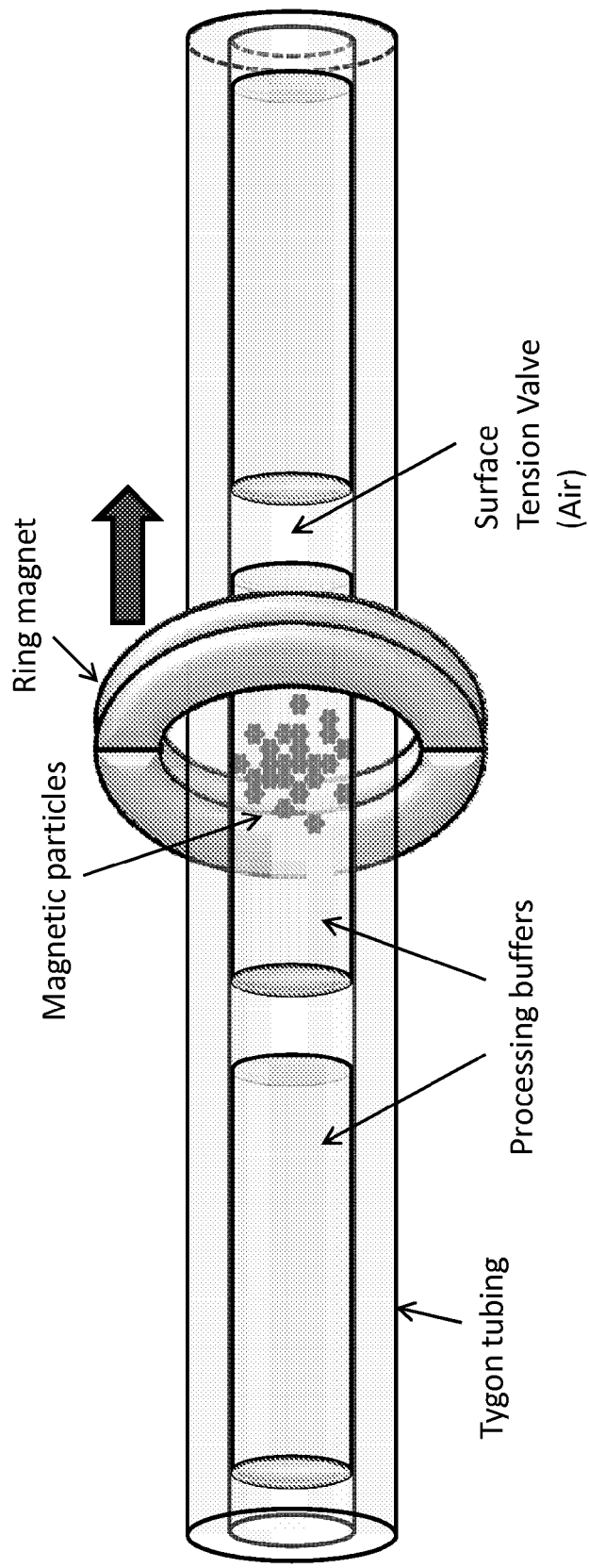
FIG. 2—Magnetic ring device "pull-through" embodiment. Design of the continuous tubing extraction cassette showing individual processing solutions separated by surface tension valves. An external magnet is used to pull RNA adsorbed to silica-coated magnetic particles through each processing solution. Following processing, the RNA is eluted in a final water chamber.

Referring to FIG. 2, a doughnut shaped magnetic is manually passed along the tubing and this transports magnetic particles. In the inset, the arrow shows the beads attempting to pass through an air surface tension valve.

Figure 3:
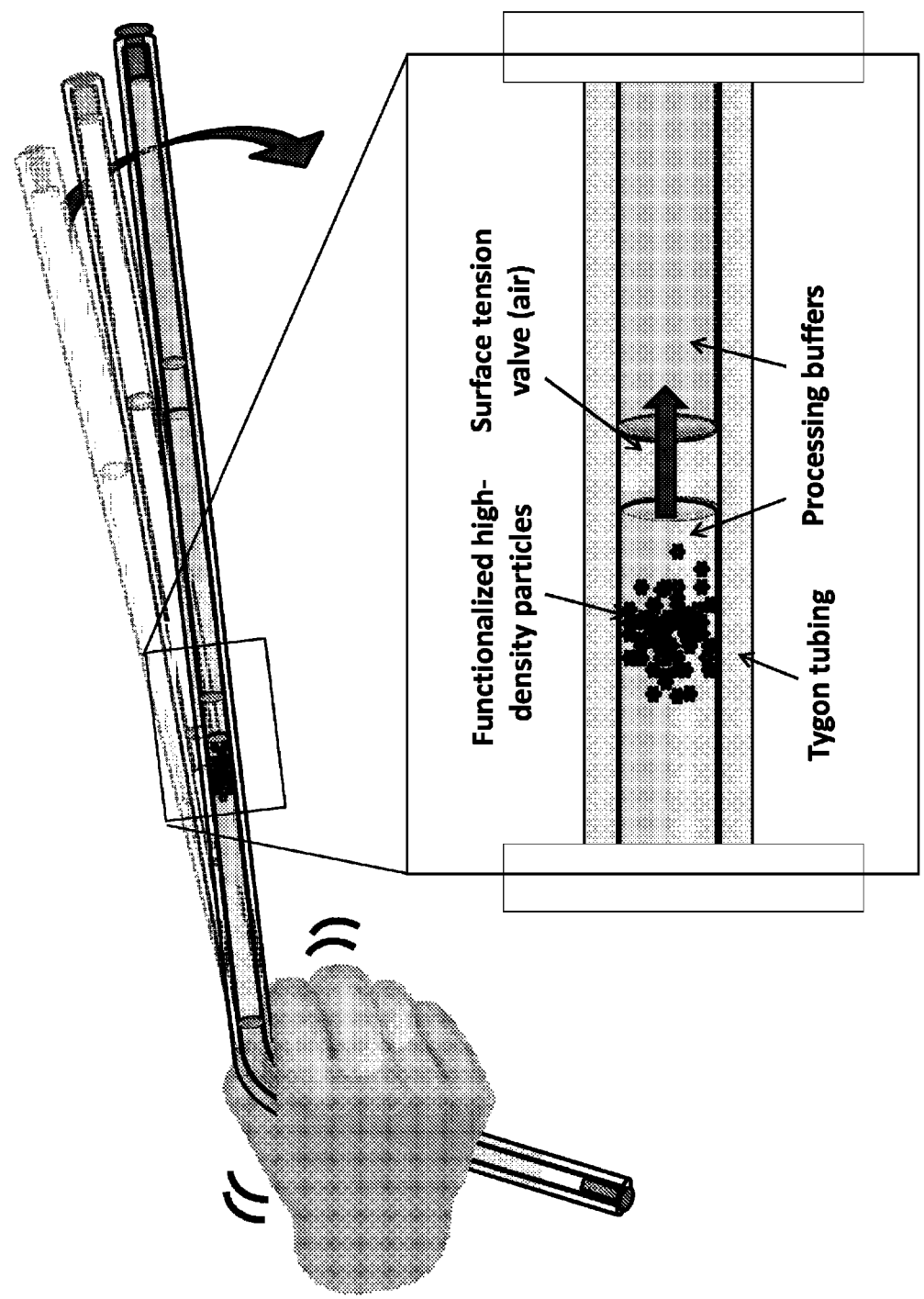
FIG. 3—Low resource processor based on centrifugal force transport of dense beads outward along the extraction cassette.

Referring to FIG. 3, the user is shown driving high density particles down the tubing with hand generated centrifugal force. In the inset, the arrow shows the beads attempting to pass through an air surface tension valve.

Figure 4:
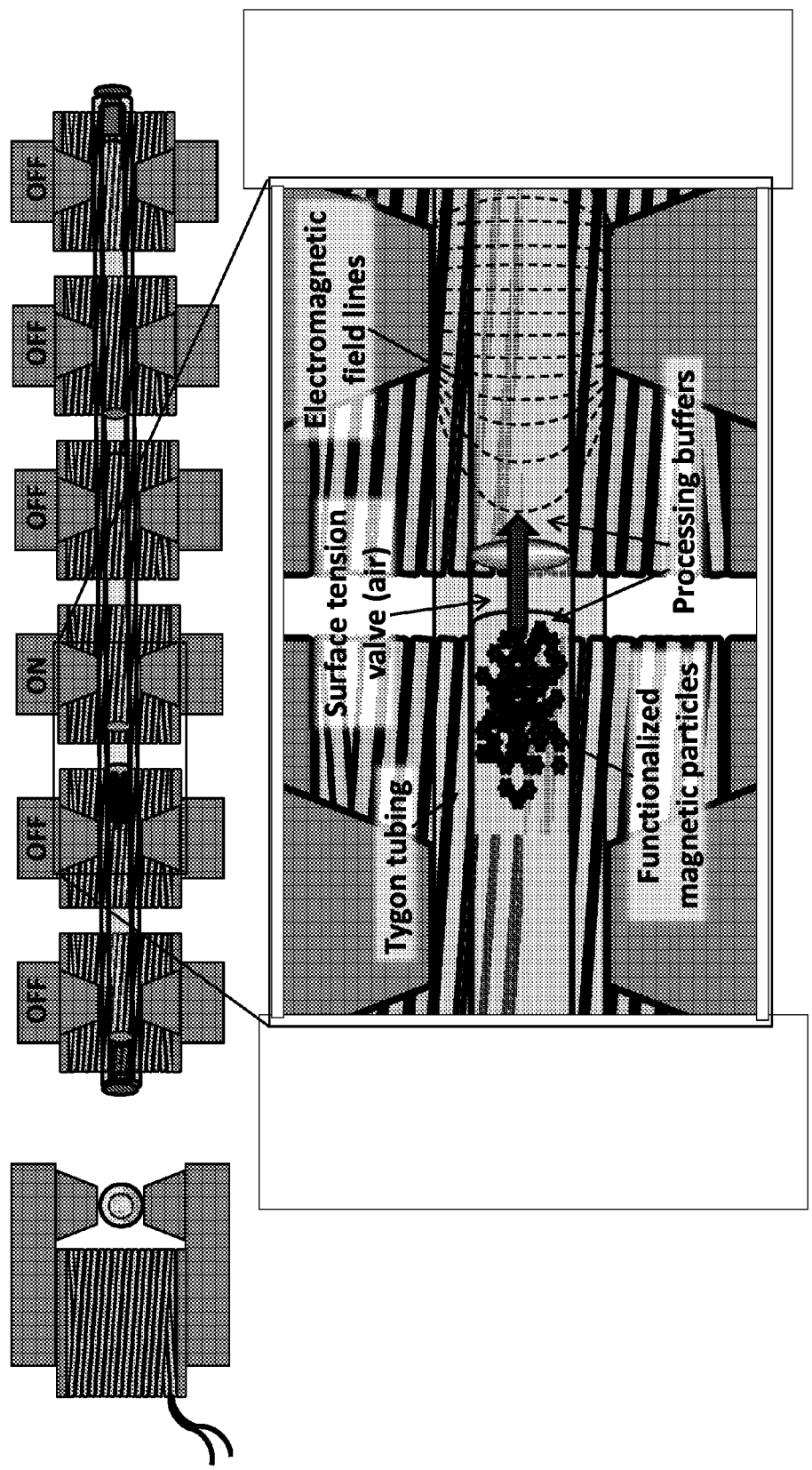
FIG. 4—Automated processor design. Views of an electromagnetic design for transporting magnetic particles from one processing solution to the next. Series of 6 electromagnets arranged in a linear array around a closed tube. Electromagnetics are turned on and off the create transient magnetic fields for pulling the magnet beads across the surface tension interface separating successive processing solutions.

Referring to FIG. 4, a series of c-clamp electromagnets are disposed along the tubing. By subjecting the electromagnets to sequential activation, the magnetic particles are transported along the length of the tubing. In the inset, the arrow shows the beads attempting to pass through an water/air surface tension valve.

Reaction Chambers.

One type of chamber is a reaction chamber. In a reaction chamber, the analyte associate with the reactant on the surface of the particle. Such a reaction chamber would be unnecessary in an embodiment where the particles are mixed with a sample prior to introduction into the device. Generally, a reaction chamber will provide suitable conditions under which the reactant on the particle and the analyte may interact. The reaction chamber may optionally include agents to inhibit non-specific interactions or to stabilize interactions once achieved.

Processing Chambers.

A variety of different types of chambers may be used in accordance with the present invention. It also is possible, where convenient, to have a series of processing chambers. A processing chamber may also be reused in the sense that the flow of the particles may be reversed so that a given chamber is used more than once. The present invention may also utilize multiple processing chambers where different solutions included therein.

One example processing chamber is a pretreatment chamber. It is often the case that reactants, samples or particles will be "pretreated" in such a way as to ensure that the ensuing reaction with the target has a high degree of fidelity, i.e., minimize non-specific attachment. A classic example is of a pretreatment is a "blocking" reaction. Non-specific protein-protein interactions by inhibited by pretreating a substrate with a non-specific protein such as BSA. Similarly, non-specific DNA reactions can be reduced by incubating the probe with a "random" DNA known to lack homology with the probe. In this case, a pretreatment chamber will proceed a reaction chamber.

Another important step when assessing the reaction of biomolecules is to remove non-specifically bound molecules from the reactant. Though achieving the same goal as pretreatment, washing takes place after the exposure of reactant to target. Typically, wash solutions comprise a buffer similar to that used in the target solution, but lacking the target itself. Occasionally, it will be desirable to alter the chemical properties of the wash solution by, for example, changing the salt concentration or pH. Wash chambers would follow a reaction chamber.

An additional chamber may be included into which the species of interest is released during the final extraction process. This chamber's function is to provide the elution step of many extraction processes. This chamber may also effectively function as a concentrating chamber since if its volume is sufficiently small compared to the original sample volume, the number of molecular targets will be higher than in the initial sample, thus effectively concentrating this species.

In some embodiments, it may be desirable to recursively amplify signals relating to binding of target analytes to reactants, or to generate more target for reaction. There are a variety of mechanisms for accomplishing this. However, a common feature will be the need for one or more chambers, prior to or following a reaction chamber, which effect the necessary steps to achieve the amplification.

Finally, in order to increase the efficiency of the process, particles may be retrieved from downstream of processing chambers and be returned to an upstream reaction or processing chamber, either by extraction and reintroduction or by reversal of the transport mechanism (e.g., centrifugal force, density or magnetic). By repeating the reaction and/or processing steps, one can increase both the signal and specificity of binding and detection.

Figure 5:
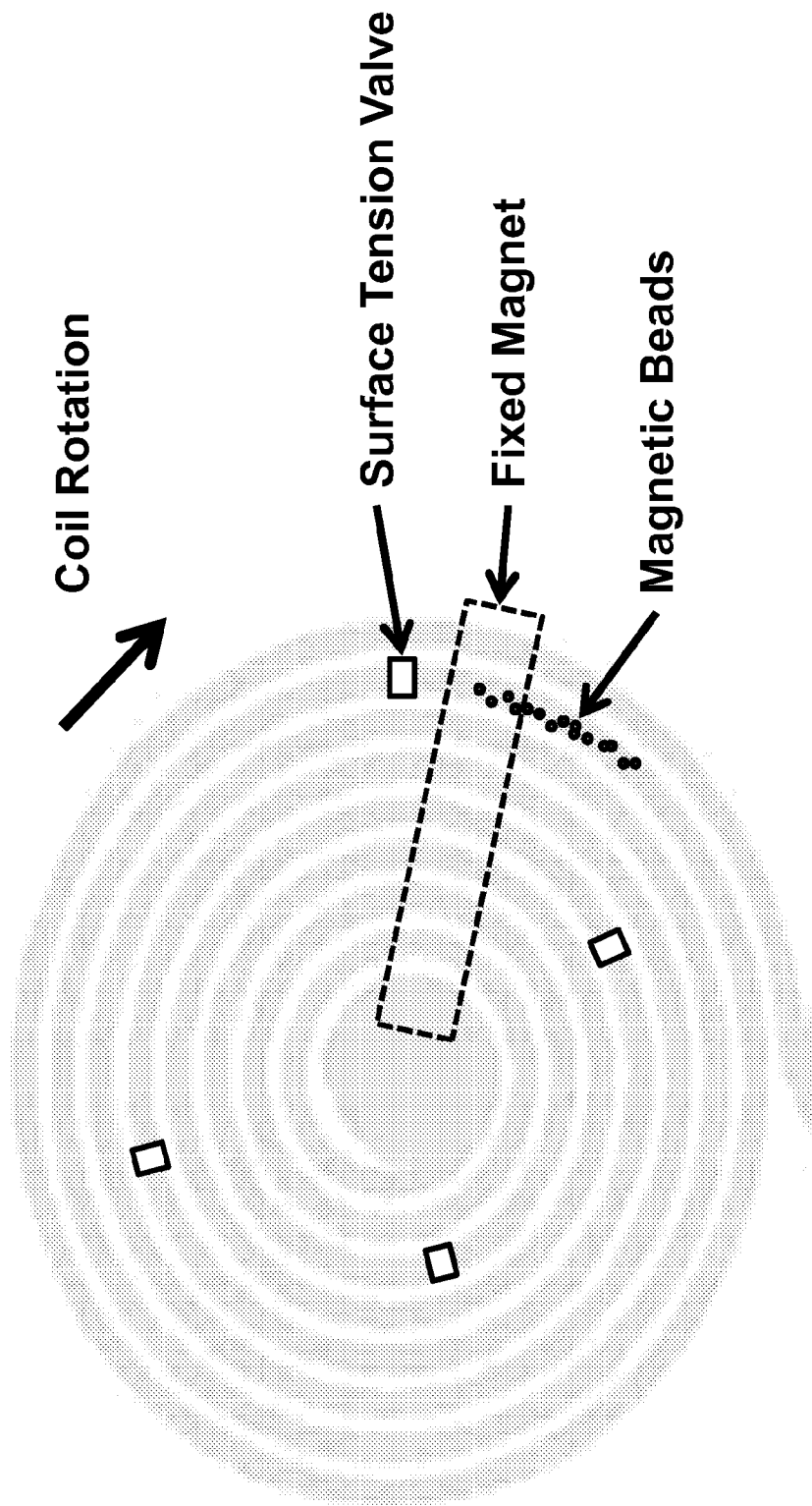
FIG. 5—Automated processor design. Top view of a coiled processor design. Fluid filled tubing contains four surface tension valves separating the five processing solutions. The coil is rotated under a fixed magnet and the magnetic beads are moved by the magnetic field through a series of processing solutions.

Thus, FIGS. 1-4 show embodiments of chambers arrayed in linear array. Tubing may also be flexible and as shown in FIG. 5 an additional embodiment may be flat coiled design which shows the tubing arrayed a coil which slowly rotates to pull the magnetic particles from one chamber to the next.

3. Surface Tension Valves

An important aspect of the invention is the use of surface tension valves to separate the tubing into discrete chambers. These surface tension valves allow flexibility in the composition of the processing fluids and the movable substrate.

In essence, the surface tension valve is simply a nonreactive gas or liquid that separates various sections of the device by creating a stable interface with the fluids that make up the various chambers. Important aspects of the gas or liquid include low vapor pressure or low surface tension, which are defined as having a vapor pressure significantly less than 1 kPa and a surface tension between 2 and 100 mN/m, including about 72 for air/water, about 50 for water/mineral oil, and about 3.3 for benzyl alcohol/water (values are from Handbook of Organic Solvents) (Lide, 1995) (incorporated by reference). Examples of appropriate gases include air, carbon dioxide, nitrogen, argon, helium, or sulfur hexafluoride. Liquids include Mineral oil, Dodecane, 1-Dodecene, Tridecane, Methyloleate, Acetophenone, Propyl Benzoate, or 1-Methylnaphthalene. Also, addition of certain materials can alter the surface tesion interface, e.g., Tween® can lower the surface tension.

There a number of ways that transport of the particles across the surface tension valve can be achieved as illustrated in FIGS. 1-5. For example, an external permanent magnet, an external movable electromagnet, centripetal force applied by tube motion around one end, and density driven (i.e., a heavy particle falling under gravity or a buoyant particle moving upward in less dense fluid).

4. Particles

The particles for use in the present invention combines the functionalities of preferential binding to a class of molecules or to a select target of interest, susceptible to transport by external force (e.g., magnet, or density differences), and small size to increase reaction efficiencies.

The particles may be synthesized of a variety of materials, such as metal, ceramic, glass, or a polymer. In particular, the particles are magnetic or paramagnetic particle for embodiments where magnetic fields are employed. In embodiments where centrifugal force is applied, he particle should have a density of >1.

Commercially available particles include those provided by SIGMA-ALDRICH and include polystyrene, polystyrene monodisperse, magnetic, melamine resin, melamine resin-carboxylate modified, polymethacrylate and silica (including beads coated with any of the foregoing substances).

Figure 6:
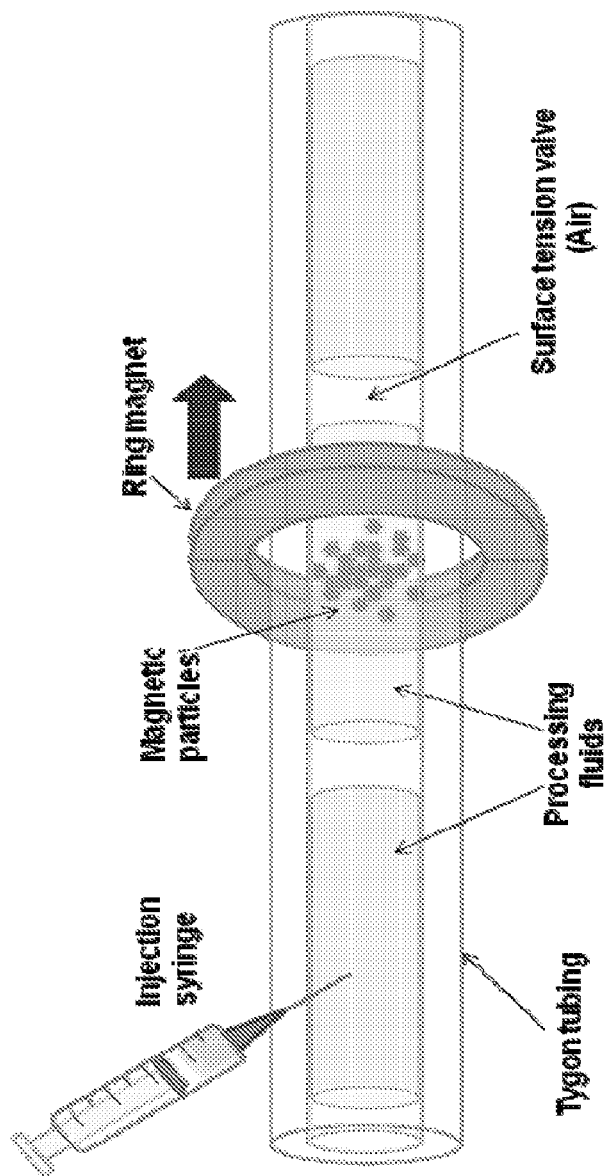
FIG. 6—Low resource point-of-care extraction processor illustrating the use of surface tension valves (in this case liquid/air interfaces) to separate liquid processing steps. A biological sample is injected into the left chamber (syringe) followed by movement of silica-coated magnetic beads from this chamber into the second using an external ring magnet. In this illustration, the captured material is released in the final chamber on the right.
Figure 7:
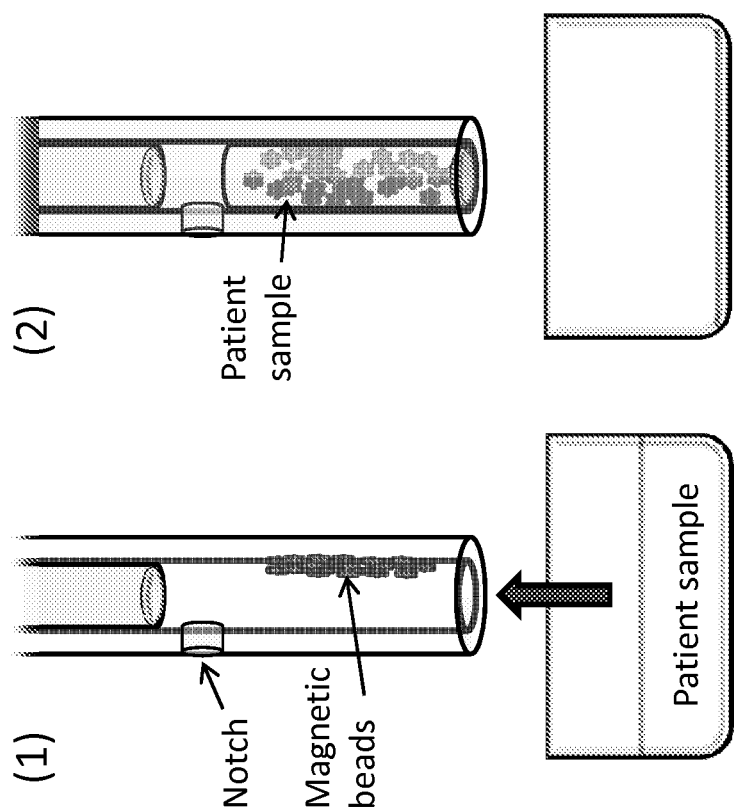
FIG. 7—Extraction cassette loading design. Method of introducing a patient sample into one end of an extraction cassette. (1) the end of the cassette is lowered into the patient sample and capillary action draws the patient sample up into one end of the cassette (2) where it interacts with magnetic beads dried on the inner surface of the tube. An external magnet is then used to transport the beads through the surface tension valves and processing solutions contained in the upper section of the tubing.

Introduction of the particles/sample into the cassette may be achieved in a number of methods. FIG. 6 illustrates injection of a sample through the wall of Tygon tubing. Particles may be mixed with the sample before injection or particles may be already present either in suspension or dried within the first section of tubing. FIG. 7 illustrates a second embodiment for loading particles/sample through capillary action. In this embodiment capillary forces present in small diameter tubes results in drawing up of the sample into the first section of the cassette. Particles may be mixed with the sample before being draw up or dried along the first section tubing in which case they are released when they come into contact with the advancing fluid. Transport of particles among the following chambers proceeds as described above.

5. Kits

According to the present invention, there are provided kits containing the devices described above. Generally, kits comprise separate vials or containers for the various reagents, such as particles, reactants, and detection reagents—either as liquids or as lyophilized solids. In the case of the latter, suitable solvent may be included such as water, ethanol, various buffer solutions, and the like. The reagents may also be provided in the device in a ready used form, i.e., with chambers and surface tension valves already established in the device. The device, particles, reactants and/or reagents may be disposed in vials or containers held in blow-molded or injection-molded plastics, or in tubing coiled within a flat circular cassette.

B. Reactants and Targets

Another important aspect of the invention is the reactants which are disposed on the surface of the particles, and the targets with which these reactants interact. By reactant, it is not necessary that the material interact in any particular type of way. Rather, any physical interaction that permits association of reactant with target analyte is envisioned, such as covalent, non-covalent, electrostatic, hydrostatic, or ionic. For example, by coating a particle with silica, one can absorb nucleic acids (DNA and RNA, depending on the solution) to the particle to the exclusion of other biomolecules. Molecules that coordinate metals, in particular heavy metals, are also envisioned as reactants. Nickel and cobalt are in particular contemplated. One can also use non-specific binding to pull out a more general class of compounds based simply on their relative interaction with the reactants.

As discussed above, the reactants can be any of a wide variety of biomolecules including nucleic acids (DNAs, RNAs), proteins. Other reactants include amino acids and small organic molecules. For two nucleic acids, the binding interaction will generally be characterized by hybridization, achieved by homologous base pairing. For one or more protein molecules, the interaction will generally be the formation of protein-ligand complexes which are reliant on the complementary structure and charge of the component molecules, such as antibody-antigen interactions and enzyme-substrate interactions. Various types of molecules suitable for use in accordance with the present invention are described below.

1. Nucleic Acids

The term "nucleic acid" is well known in the art. A "nucleic acid" as used herein will generally refer to a molecule of DNA, RNA or a derivative or analog thereof, including synthetic molecules. Nucleic acids are also defined as molecules containing a series of naturally-occurring purine or pyrimidine bases. The term "nucleic acid" encompasses the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length.

These definitions generally refer to both single-stranded and double-stranded molecules, the latter being substantially or fully complementary to each other. A nucleic acid may even encompass a triple-stranded molecule. As used herein, a single stranded nucleic acid may be denoted by the prefix "ss," a double-stranded nucleic acid by the prefix "ds," and a triple stranded nucleic acid by the prefix "ts."

(b) DNA

DNAs are defined as nucleic acids containing adenine "A," guanine "G," thymine "T" and cytosine "C." DNA molecules, both single- and double-stranded, may be utilized in accordance with the present invention. DNAs may comprise coding sequences or non-coding sequence, and genomic sequences or cDNAs, synthesized strands homologous to the target of interest. DNA "arrays"—collections of DNAs that represent a group of selected probes.

(c) RNA

RNAs are defined as nucleic acids containing A, G, uracil "U" or C. Both single- and double-stranded RNAs, may be utilized in accordance with the present invention. Because of their labile nature, additional steps must be take to preserve the integrity of RNA containing samples. In particular, the ubiquitous presence of RNAses requires the use of RNAse inhibitors such as DEPC.

2. Proteins

In another embodiment, the probe may be a proteinaceous compound. There are wide variety of protein-protein interactions; however, proteins also bind nucleic acids, metals and other non-proteinaceous compounds (e.g., lipids, hormones, transmitters). Some examples of protein that may be used as either targets or probes are listed below.

(a) Antibodies

Antibodies may be used as probes for unknown molecules, or they maybe the target for reaction with a known probe. The antibodies may be either polyclonal or monoclonal in origin. Method for preparing antibodies are well known to those of skill in the art and need not be discussed here. Antibodies may be fixed to the filament support using standard techniques.

Obviously, identifying antibodies that bind to certain target molecules is an important goal that could be accomplished by the present invention. However, the present invention also permits the screening of samples for the presence of antibodies. For example, a particle might contain a variety of bacterial and viral antigens, which could assist in diagnosis of infectious disease by identifying relevant antibodies in an affected subject.

(b) Enzymes

Enzymes are proteins that facilitate the modification of a wide variety of compounds including nucleic acids, other proteins, lipids, sugars, steroids and many other compounds. Particular types of assays contemplated include identifying inhibitors of enzymes that bind to, but are not processed by, the enzyme. Alternatively, identifying compounds that are bound by an enzyme may assist in design of pro-drugs that are processed by an enzyme.

(c) Receptors

Receptors are molecules that facilitate signaling processes by binding their cognate ligand moieties. Once bound, the receptor will then perform some other function (enzymatic, intracellular translocation, cell permeability) that effects the signaling. Identifying molecules that block receptor function, or mimic the natural ligand, can be accomplished using the present invention.

(d) DNA-binding proteins

Another important class of proteins is the DNA binding proteins. These proteins include polymerases, helicases, ligases, and transcription factors. The proteins have varying degrees of DNA sequence specificity can be assessed for ability to bind varying DNA sequences. Conversely, providing a DNA sequence as a probe, once can identify unknown binding proteins with specificity for that sequence.

3. Small Molecules and Other Targets

A wide variety of "small molecules" can be examined for their ability to interact to a given reactant. These libraries comprise non-protein and non-nucleic acid molecules. Alternatively, libraries can be constructed around particular "pharmacores" that are believed to provide basic structural features necessary for a particular drug to function.

Also, compounds such as liquids, carbohydrates, metals, and toxins may be assayed using the devices and methods of the present invention.

4. Labels

In various embodiments, it may desirable to label particles, reactant, or target molecules. Examples of labels include paramagnetic ions, radioactive isotopes, chemiluminescent compounds, fluorophores, chromophores, NMR-detectable substances, and X-ray imaging compounds.

Paramagnetic ions include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

Radioactive isotopes include astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine $^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection.

Among the fluorescent labels contemplated for use include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Enzymes (an enzyme tag) that will generate a colored product upon contact with a chromogenic substrate may also be used. Examples of suitable enzymes include urease, alkaline phosphatase, (horseradish) hydrogen peroxidase or glucose oxidase. Preferred secondary binding ligands are biotin and/or avidin and streptavidin compounds. The use of such labels is well known to those of skill in the art and are described, for example, in U.S. Pat. Nos. 3,817,837; 3,850,752; 3,939,350; 3,996,345; 4,277,437; 4,275,149 and 4,366,241; each incorporated herein by reference.

C. Definitions

The terms a or an, as used herein, are defined as one or more than one.

The term plurality, as used herein, is defined as two or more than two.

The term another, as used herein, is defined as at least a second or more.

The terms including and/or having, as used herein, are defined as comprising (i.e., open language).

The term coupled, as used herein, is defined as connected, although not necessarily directly.

The term approximately, as used herein, is defined as at least close to a given value (e.g., preferably within 10% of, more preferably within 1% of, and most preferably within 0.1% of).

The term substantially, as used herein, is defined as at least approaching a given state (e.g., preferably within 10% of, more preferably within 1% of, and most preferably within 0.1% of).

The phrase "any integer derivable therein," as used herein, is defined as an integer between the corresponding numbers recited in the specification, and the phrase any range derivable therein is defined as any range within such corresponding numbers.

D. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—RSV RNA Extraction

Figure 8:
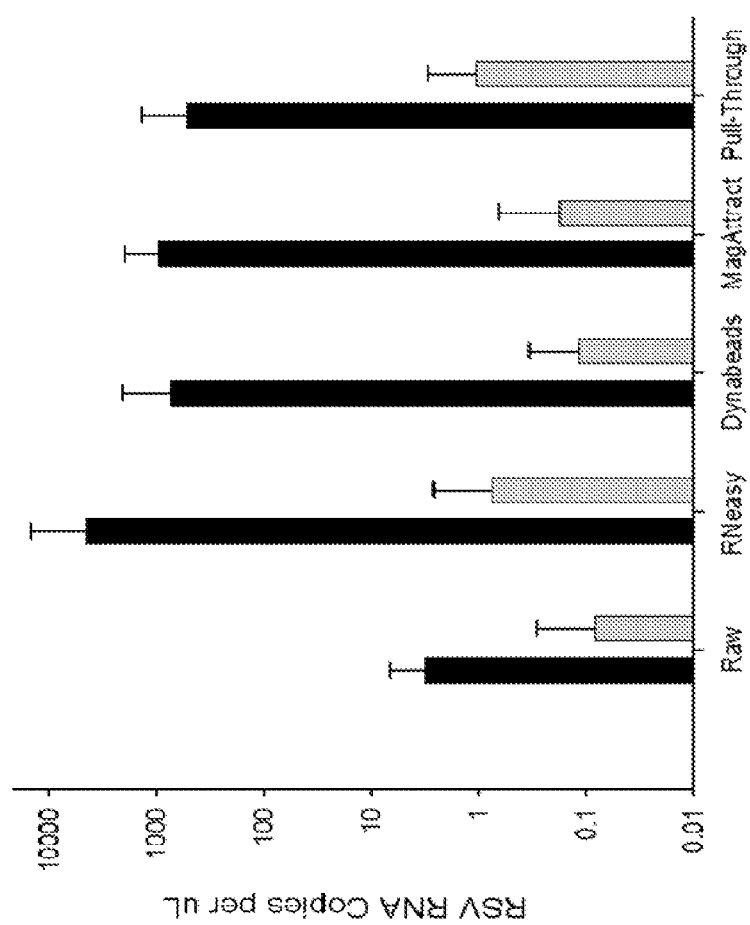
FIG. 8—RSV RNA extraction using low resource pull-through RNA extraction device (right columns) is comparable to commercially available kits. Comparison of RSV RNA extraction from 7 RSV+ (black bars) and 7 RSV− (grey bars) stored pediatric nasal wash samples using five methods. Extraction using magnetically driven pull-through design had an extraction efficiency similar to two of the three commercially available kits. Mean±S.D>, N=7.

One embodiment of this idea is shown in FIG. 6 which illustrates one design for extracting viral RNA from pediatric nasal wash samples. Lysed nasal wash sample is injected through the wall of the Tygon tubing into the first chamber on the left and mixed with silica-coated magnetic particles in guanidine salt buffer present in this chamber. Sample RNA binds to the silica surface. Pre-loaded processing solutions are held in place by the surface tension forces of the valves. Magnetic beads are entrained by an external magnet and pulled through each of the processing solutions. Surprisingly when the beads reach the liquid-air interface they pass through it without entraining solution. Entry into the next solution proceeds similarly until the entire cloud of particles passes through all of the process steps. Processing removes sample contaminants, and RNA is concentrated in 50 µl of water in the final chamber and used in downstream RT-PCR processing to detect the presence of respiratory syncytial virus (RSV). FIG. 8 shows a comparison of RSV RNA extraction using the magnetic pull-through design and several commercial kits.

RNA Extraction from TE Buffer and HEp-2 Cell Lysates Using Continuous Tubing Extraction Cassette.

The initial prototype design of FIG. 1 was further simplified into a continuous tubing design shown in FIG. 2. In this design, 8 processing solutions were preloaded within ~61 cm length of Tygon tubing (1.6 mm i.d.). These solutions were chaotropic wash buffer (300 µL of 4 M guanidine hydrochloride, 25 mM sodium citrate, pH 7.0), two sections containing RNA precipitation buffer (300 µL of 80% ethanol, 5 mM potassium phosphate, pH 8.5), three sections containing a water wash (100 µL of molecular grade water), and RNA elution (50 µL of molecular grade water). The 50 µL elution volume was chosen so that the RT-PCR input would be comparable to other extraction methods such as the RNeasy kit. Each solution was separated from the next by an air gap ~2 mm in length. Three types of extraction test samples were prepared: 5 µL of RSV N gene standard RNA in TE buffer at a concentration of $1\times10^6$ copies/µL, 20 µL of HEp-2 cell lysates ($2\times10^3$ cells/µL) spiked with 5 µL of RNA standard, or 20 µL of RSV infected HEp-2 cell lysates. Cell lysate samples were homogenized by passage through a 25 gauge needle five times. Prior to extraction, samples were added to 230 µL of RNA-silica binding buffer (230 µL of 2 M guanidine thiocyanate, 25 mM sodium citrate, pH 7.0, 50% ethanol) and 20 µL of silica-coated 1 µm diameter magnetic particles ($3\times10^6$ particles/µL) (Bioneer Inc., Alameda, Calif.) and placed on a rotating mixer for 5 minutes at room temperature. After mixing, each sample was loaded into the tubing, and the tubing ends were capped. The particles were collected in the first chamber by the external magnet and pulled through the surface tension valves and each successive chamber at ~4 mm/second using ~5 cm diameter neodymium ring magnet (Emovendo LLC, Petersburg, W. Va.) as depicted in FIG. 2. Particles were dispersed in the chaotropic wash and RNA precipitation solutions by rapidly moving the magnet back and forth before being recollected. In the water wash solutions, the particles were moved at ~8 mm/second to minimize RNA loss by elution during the wash. Finally, the particles were dispersed in the final elution chamber and incubated at room temperature for 5 minutes before removal. Although it was utilized in the prototype design, the elution of RNA at 65° C. was not performed in this final design because it would be impractical in most low resource settings. The final chamber contents were collected for RT-PCR analysis. Each RNA extraction was completed in ~15 minutes.

Figure 9:
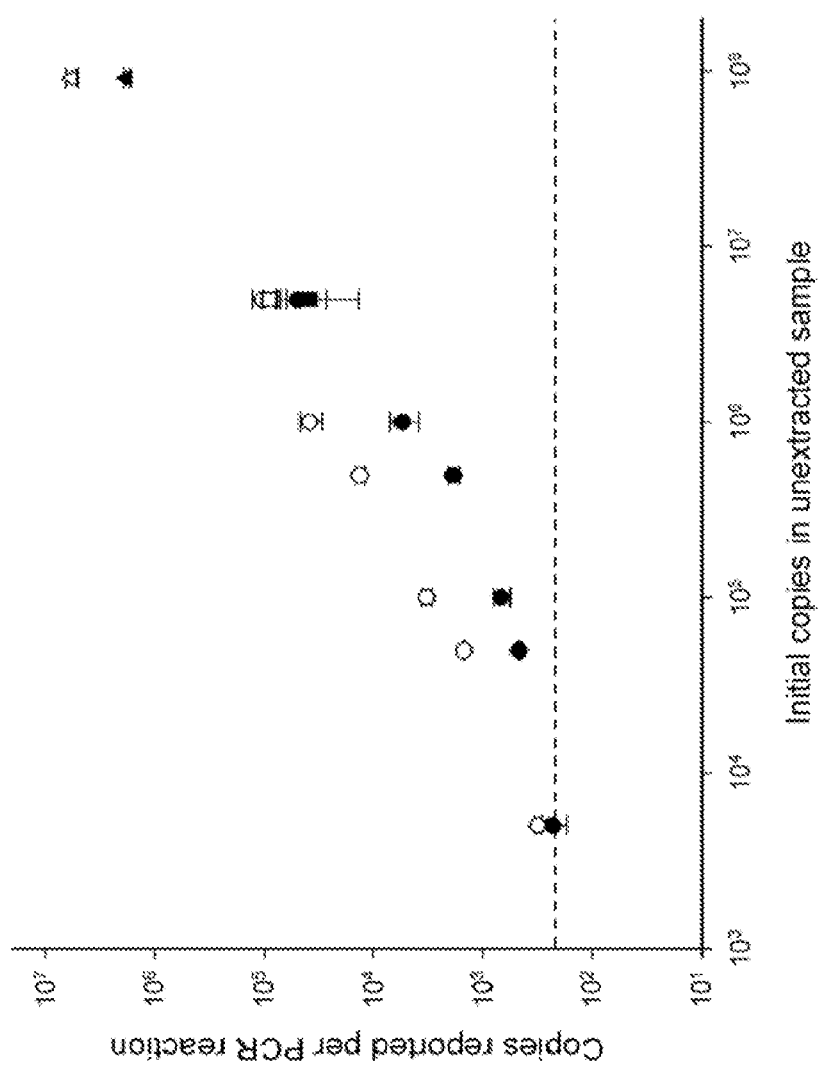
FIG. 9—The limit of detection of RNA detectable by RT-PCR after extraction from HEp-2 cell lysates spiked with known amounts of RSV RNA using either the continuous tubing extraction cassette (•) or the RNeasy kit (o) (mean±s.d, n=3). When a sample containing no copies of RNA was extracted, 197±8.5 RNA copies were detected with the extraction cassette and 202±9.5 copies were detected with the RNeasy kit. The limit of detection is shown for the continuous tubing extraction cassette (dotted line). The extraction cassette limit of detection was determined by calculating the minimum quantity of target RNA that must be added to RSV negative cell lysates to be detectable by RT-PCR following extraction. This value was compared to the limit of detection calculated for the RNeasy kit. Twenty µL of uninfected HEp-2 cell lysate was spiked with 5 µL of RNA in TE buffer containing 0, $5\times10^3$, $5\times10^4$, $1\times10^5$, $5\times10^5$, $1\times10^6$, and $5\times10^6$ copies of RSV N gene RNA standard and extracted by both methods as described in section 2.6. After extraction, the RNA was quantified by RT-PCR. The limit of detection was defined as 3 s.d. above the mean value obtained for control extractions containing no RNA.

An example of the operating characteristics of this design is illustrated in FIG. 9. The limit of detection of RNA detectable by RT-PCR after extraction from HEp-2 cell lysates spiked with known amounts of RSV RNA using either the continuous tubing extraction cassette (•) or the RNeasy kit (o) (mean±s.d, n=3). When a sample containing no copies of RNA was extracted, 197±8.5 RNA copies were detected with the extraction cassette and 202±9.5 copies were detected with the RNeasy kit. The limit of detection is shown for the continuous tubing extraction cassette (dotted line). The extraction cassette limit of detection was determined by calculating the minimum quantity of target RNA that must be added to RSV negative cell lysates to be detectable by RT-PCR following extraction. This value was compared to the limit of detection calculated for the RNeasy kit. Twenty uL of uninfected HEp-2 cell lysate was spiked with 5 µL of RNA in TE buffer containing 0, $5\times10^3$, $5\times10^4$, $1\times10^5$, $5\times10^5$, $1\times10^6$, and $5\times10^6$ copies of RSV N gene RNA standard and extracted by both methods. After extraction, the RNA was quantified by RT-PCR. The limit of detection was defined as 3 s.d. above the mean value obtained for control extractions containing no RNA.

Example 2—Transrenal DNA Extraction

In this example, four processing solutions were preloaded within ~45 cm length of Tygon tubing having an inner diameter of 1.6 mm. These solutions were chaotropic wash buffer (300 µL of 4 M guanidine hydrochloride, 25 mM sodium citrate, pH 7.0), two sections containing DNA precipitation buffer (300 µL of 80% ethanol, 5 mM potassium phosphate, pH 8.5), and DNA elution (50 µL of molecular grade water). These solutions were separated from one another by an air gap ~2 mm in length.

A 140 base DNA sequence from the IS6110 sequence of Mycobacterium tuberculosis was synthesized by Integrated DNA Technologies (Coralville, Iowa), and $5\times10^7$ copies were spiked into 200 µL of synthetic urine composed of (in g/L) 0.65 calcium chloride dihydrate, 0.65 magnesium chloride, 4.6 sodium chloride, 2.3 sodium sulfate, 0.65 sodium citrate dehydrate, 2.8 potassium phosphate dibasic, 1.6 potassium chloride, 1.0 ammonium chloride, 25 urea, and 1.1 creatinine (Miro-Casas et al., 2001). The DNA-spiked synthetic urine samples were mixed with 200 µL of DNA-silica binding buffer (4 M guandidine thiocyanate, 25 mM sodium citrate, pH 7.0) and 20 µL (0.8 mg) of Invitrogen Dynabeads MYONE silane beads (Carlsbad, Calif.) and vortexed for 5 minutes at room temperature. After mixing, the sample was loaded into the tubing, and the tubing ends were capped. The particles were collected in the first chamber by the external magnet and pulled through the air valves and each successive chamber at ~4 mm/second using ~5 cm diameter neodymium ring magnet (Emovendo LLC, Petersburg, W. Va.). Particles were dispersed in the chaotropic wash and DNA precipitation solutions by rapidly moving the magnet back and forth before being recollected. Finally, the particles were fully dispersed in the DNA elution chamber and removed, and the final chamber contents were collected for PCR analysis. Each DNA extraction was completed in ~9 min. The extraction efficiency was compared to DNA extracted using the Qiagen DNeasy kit according to manufacturer's instructions.

A 129 base fragment of the IS6110 sequence was amplified using forward primer 5'-ACCAGCACCTAACCGGCT-GTGG-3' (SEQ ID NO:1) and reverse primer 5'-CATCGTG-GAAGCGACCCGCCAG-3' (SEQ ID NO:2) (Cannas et al., 2008). Reactions were performed in a 25 µL volume using 5 µL of DNA template and the Qiagen Quantitect SYBR green PCR kit according to manufacturer's instructions. Thermal cycling consisted of 94° C. for 15 minutes to activate DNA polymerase, and 40 cycles of 94° C. for 15 s, 62° C. for 30 s, and 72° C. for 30 s using a Rotor-Gene Q thermal cycler (Qiagen, Germantown, Md.). Product specificity was confirmed using melting curve analysis. Data was collected and $C_t$ values recorded by Rotor-Gene Q Software (Qiagen, Germantown, Md.) and converted to number of copies of DNA per µL using a standard curve.

Figure 10:
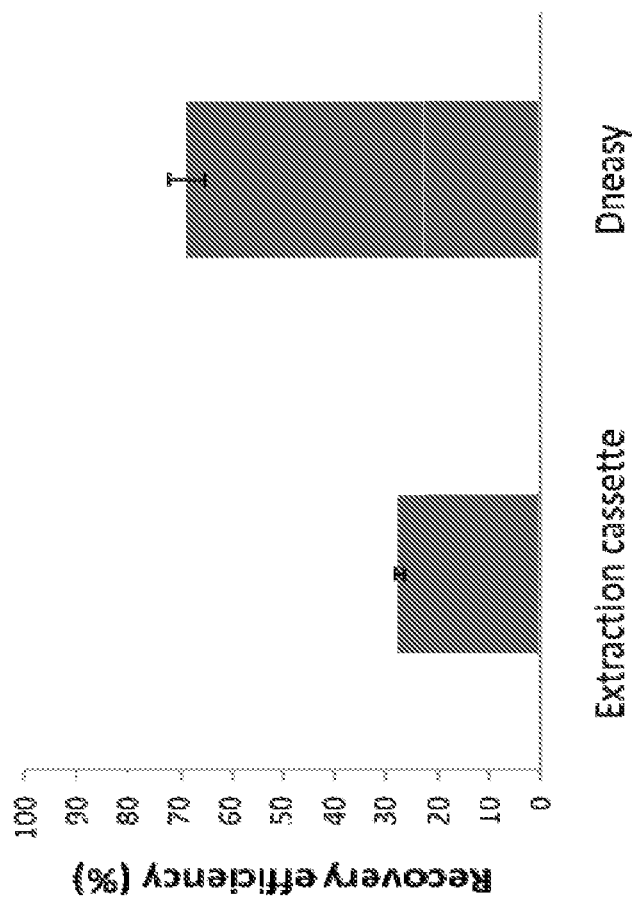
FIG. 10—DNA extraction. Comparison of the percent of the tuberculosis target IS6110 DNA recovered from 200 µL of synthetic urine using the extraction cassette (left bar) and DNeasy kit (right bar), (mean±s.d., n=3).

FIG. 10 illustrates results using this embodiment. DNA extracted from spiked synthetic urine was recovered at an efficiency of 27.15±1.10%. This corresponded to a DNA elution concentration of 271,500±11,020 copies/µL. DNA extracted using the DNeasy kit was recovered with an efficiency of 68.6±3.48%. The corresponding DNA elution concentration was 686,000±34,780 copies/µL. Recovery efficiency was calculated by dividing the total number of extracted copies by the initial number of copies present in the sample and multiplying by 100%.

Example 3—Protein Isolation Using Air/Liquid Interface

With a strip of Tygon® tubing cut to 9.5" in length, laid horizontally on the benchtop, insert 10 µL of Buffer B (50 mM sodium phosphate pH 8.0, 300 mM NaCl, 500 mM imidazole, 0.05% Tween-20) into the right end of the tubing using a gel tip pipette tip and seal that end with the rounded end of the MelTemp capillary tube (only insert the glass ⅛" into the Tygon® tubing). Fill a 1 mL syringe with Buffer A (50 mM sodium phosphate pH 8.0, 300 mM NaCl, 200 mM imidazole, 0.05% Tween-20). Carefully remove all air bubbles from the syringe cylinder and needle and dispense buffer until black syringe cap rests at the 1 mL tick mark. ⅛" from the left side of the elution chamber insert the syringe needle into the wall of the tubing and dispense 0.1 mL of Buffer A. ⅛" from the left side of the above wash chamber, insert the syringe again into the wall of the tubing and dispense 0.1 mL of Buffer A. Repeat a third time to yield 3 wash chambers. Insert the cut end of a PCR tube (that has been cut at the rounded end to have a small circular opening) into the right hand side of the tubing, making sure the Tygon® tubing completely seals around the bottom of the tube and there are no puckers or creases in the PCR tube. Using a syringe needle, puncture a small hole into the cap of the tube to serve as a release valve.

Holding the extraction tubing upright, pipette 100 μL of sample into the PCR tube followed by 100 μL of Buffer C. Ensure proper mixing of the sample to fully lyse all cells. To the loading chamber containing the lysed sample, add 10 μL of 100× diluted Dynabeads® to the PCR tube. Close the cap and seal the hole with a small piece of tape. Lay the tubing on the rotisserie (affix to rotisserie using tape if necessary) and allow the tubing to rotate for 10 minutes in order to properly mix the sample. After 10 minutes, remove the tube from the rotisserie. Collect the beads into a pellet at the cut end of the PCR tube using the donut magnet. Pull the beads through the first air valve and into the first wash chamber. Disperse the beads for one minute using a "back and forth" motion along the length of the chamber. Collect the pellet of beads at the end of the first wash chamber, and then pull the pellet through the air valve and into the second wash chamber. In a similar fashion, pull the beads through the second and third wash chambers, ensuring that the beads are sufficiently dispersed throughout the chamber. Collect the pellet of beads in the third wash chamber, pull the pellet into the elution chamber and disperse the beads using a "back and forth" motion for 10 minutes. After 10 minutes, pull the beads back into the air chamber on the left side of the elution chamber. Using a pipette, remove the 200 μL sample from the sample loading chamber and place into a new Eppendorf® tube. Slice the air valve to the left of the elution chamber in between the bead pellet and the elution chamber with the razor. Place the sliced end of the extraction tubing into an Eppendorf® tube with the MelTemp capillary tube pointing upward. Remove the MelTemp tube and pipette 90 μL of Buffer B into the Tygon® tubing containing the elution chamber in order to flush the chamber into a fresh Eppendorf® tube. Reserve the samples for later analysis.

Figure 11:
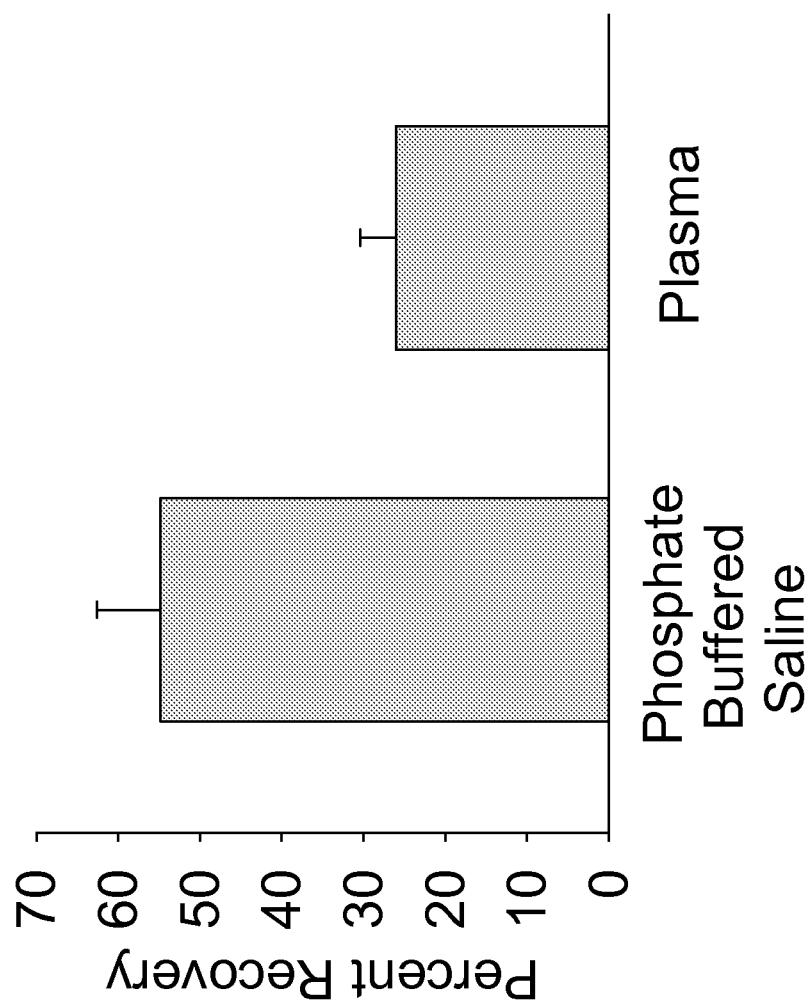
FIG. 11—Protein extraction using air valves. Histidine rich protein extraction from phosphate buffered saline and plasma. Mean+/−s.d., N=3.

FIG. 11 illustrates the extraction percentages for this example. The malaria protein target (histidine rich protein) was extracted from phosphate buffered saline and plasma at efficiencies of approximately 55% and 25%, respectively.

Example 4—Protein Isolation Using Mineral Oil/Water Surface Tension Valve

A device according to the present invention is used to isolate a surrogate target relevant to malaria (HRP-II labeled with the fluorescent compound TAMRA). Amine-terminated magnetic beads (silanized iron oxide, 12 μmol amines/mL, p=2.5 g/mL, 1-4 μm diameter, 25-35 EMU/g) were cross-linked with lysine modified NTA using $BS^3$ as the cross-linker. After crosslinking, the particles were charged with Ni(II) using $NiCl_2$. For the device, each chamber contains 100 μL of solvent. Between each chamber is ~25-50 μL of light mineral oil as the valve. Tygon tubing of 1/16 in (diameter) is utilized. The chamber content and reactions are as follows:

Chamber 1 (Sample): Sample reacted with Ni(II)NTA magnetic beads
Chamber 2 (Wash 1): 0.1 M phosphate buffer (pH 8.0), 300 mM NaCl, 0.25% Tween
Chamber 3 (Wash 2): 0.1 M phosphate buffer (pH 8.0), 300 mM NaCl, 0.25% Tween 20
Chamber 4 (Elution): 0.1 M phosphate buffer (pH 8.0), 300 mM NaCl, 0.25% Tween 20, 200 mM imidazole
Chamber 5 (Post-Elution): 0.1 M phosphate buffer (pH 8.0), 300 mM NaCl, 0.25% Tween 20, 200 mM imidazole The device was pre-loaded with chambers 2-5, divided with light mineral oil. Air pockets were avoided as much as possible. Both the target (TAMRA HRP-II, 10 μM binding sites) and BSA (fluorescein BSA, 100 μg/mL) were incubated with Ni(NTA) magnetic beads (100 μM Ni(II)NTA's) for 10 min (100 μL total volume). After incubation, the mixture was injected into the first chamber. A donut magnet was then used to transfer the magnetic beads through the tube. When the beads arrived into a chamber, they were spread out throughout the chamber by quickly moving the magnet back and forth. Next, the magnet was slowly moved across the chamber, oscillating perpendicular to the tube to ensure efficient mixing. This process takes ~1 min. The beads are then collected by the magnet and transferred to subsequent chambers. When the extraction is complete, the chambers were collected and analyzed using fluorescence.

Pull-Through Procedure (BNT-II)

The same procedure is applied to a device having a starting chamber comprising BNT-II (1 μM), BSA (40 mg/mL), 100 μM Ni(II)NTA magnetic beads.

Figure 12:
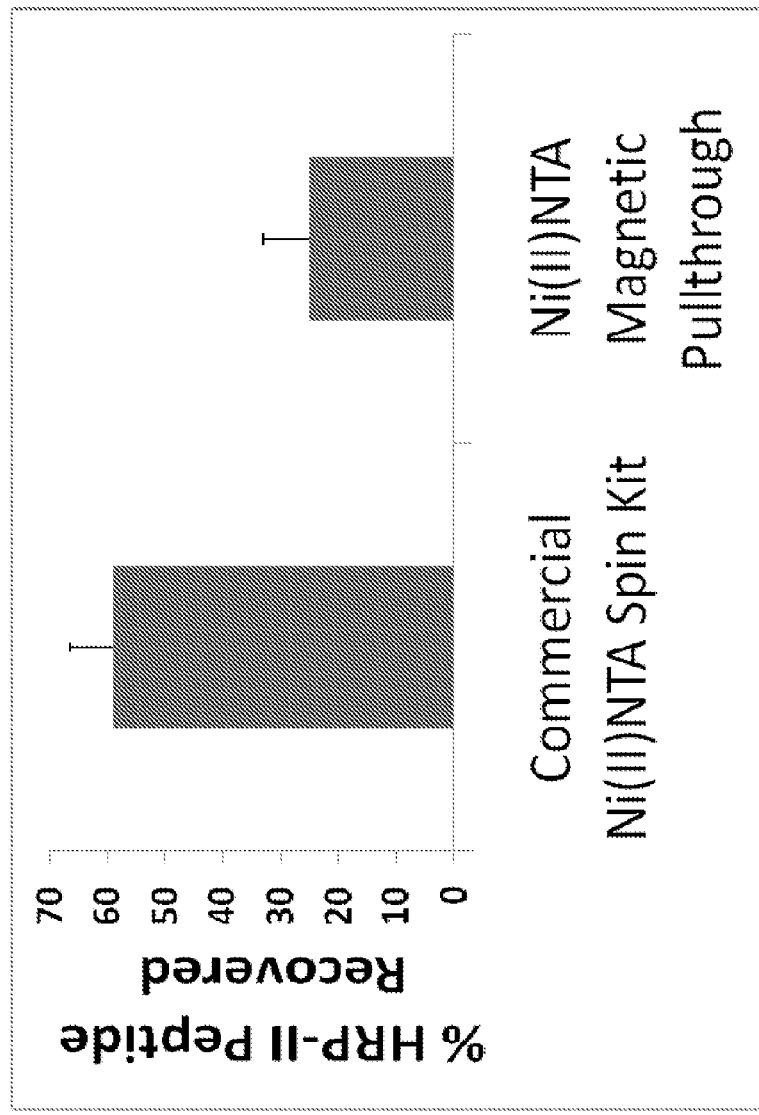
FIG. 12—Comparison of malaria protein extraction with a commercial spin column and a pull-through design. This is a simple comparison of the two methods under ideal conditions for each method. The commercial kit was performed using the standard reagents found in the kit. The % recovery is indicative of the amount of protein collected in the first elution of both methods (elution chamber for us and the first elution spin down for the spin kits) (mean±s.d., n=3).

FIG. 12 shows representative results applying the device and method as described in this example.

All the disclosed embodiments of the invention disclosed herein can be made and used without undue experimentation in light of the disclosure. The invention is not limited by theoretical statements recited herein. Although the best mode of carrying out the invention contemplated by the inventors is disclosed, practice of the invention is not limited thereto. Accordingly, it will be appreciated by those skilled in the art that the invention may be practiced otherwise than as specifically described herein.

Further, the individual components need not be formed in the disclosed shapes, or combined in the disclosed configurations, but could be provided in virtually any shapes, and/or combined in virtually any configuration. Further, the individual components need not be fabricated from the disclosed materials, but could be fabricated from virtually any suitable materials.

Further, variation may be made in the steps or in the sequence of steps composing methods described herein. It will be manifest that various substitutions, modifications, additions and/or rearrangements of the features of the invention may be made without deviating from the spirit and/or scope of the underlying inventive concept. It is deemed that the spirit and/or scope of the underlying inventive concept as defined by the appended claims and their equivalents cover all such substitutions, modifications, additions and/or rearrangements.

The appended claims are not to be interpreted as including means-plus-function limitations, unless such a limitation is explicitly recited in a given claim using the phrase(s) "means for" and/or "step for." Subgeneric embodiments of the invention are delineated by the appended independent claims and their equivalents. Specific embodiments of the invention are differentiated by the appended dependent claims and their equivalents.

E. REFERENCES

The following references to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,277,437
U.S. Pat. No. 4,275,149
U.S. Pat. No. 4,366,241

Aceti et al., *Thorax.*, 54(2):145-146, 1999.
Avison, In: *Measuring gene expression*, Taylor & Francis, NY, 2007; 324, 2007.
Beuselinck et al., *J. Clinical Microbiol.*, 43(11):5541-5546, 2055.
Bordelon et al., *ACS Applied Materials & Interfaces*, 3:2161-2168, 2011.
Bryzgunova et al., *Ann. NY Acad. Sci.*, 1075:334-340, 2006.
Cannas et al., *Int. J. Tuberc. Lung Dis.*, 12(2):146-151, 2008.
Chen et al., *Biomed. Microdevices*, 12(4):705-719, 2010.
Chirgwin et al., *Biochemistry* 18(24):5294-5299, 1979.
Chomczynski and Sacchi, *Analytical Biochem.*, 162(1):156-159, 1987.
Coiras et al., *J. Med. Virol.*, 69(1):132-44, 2003.
Gopinath and Singh, *J. Appl. Microbiol.*, 107(2):425-435, 2009
Green et al., *Lancet. Infect. Dis.*, 9(8):505-511, 2009.
Hagan et al., *Lab. Chip.*, 11(5):957-61, 2011.
Handbook of Solvents, Lide (Ed.), CRC Press, 1-565, 1995.
Huggett et al., *Biochem. Soc. Trans.*, 37(Pt 2):419-423, 2009.
MacDonald et al., In: *Methods in Enzymology*, Academic Press, 152:219-227, 1987.
Miro-Casas et al., *Anal. Biochem.*, 294(1):63-72, 2001.
Monteiro et al., *J. Clinical Microbiol.*, 35(4):995-998, 1997.
Niemz et al., *Trends Biotechnol.*, 29(5):240-250, 2011.
Price et al., *Lab. Chip.*, 9(17):2484-2494, 2009.
Radstrom et al., *Mol. Biotechnol.*, 26(2):133-46, 2004.
Umansky and Tomei, *Expert Rev. Mol. Diagn.*, 6(2):153-163, 2006.
Wilson, *Appl. Environ. Microbiol.*, 63(10):3741-3751, 1997.
Yamada et al., *J. Virol. Methods*, 27(2):203-209, 1990.

What is claimed is:

1. A method of processing a sample comprising:
   (a) providing a device comprising continuous tubing forming a plurality of sequential chambers, each of said sequential chambers comprising a fluid and separated by a non-reactive gas-based surface tension valve that permits selective passage a particle between said sequential chambers, wherein a first reaction chamber comprises a particle having a reactant on its surface;
   (b) introducing into said first reaction chamber a sample;
   (c) incubating said first reaction chamber under conditions sufficient to permit reaction of said reactant with an analyte in said sample;
   (d) transporting said particle from said first reaction chamber into at least a second chamber through said non-reactive gas-based surface tension valve disposed therebetween; and
   (e) detecting interaction of said analyte with said reactant.

2. The method of claim 1, wherein said device comprises at least three chambers.

3. The method of claim 2, wherein said device comprises said first reaction chamber, a first processing chamber and a first detection chamber, wherein said first processing chamber is disposed between said first reaction chamber and said first action chamber.

4. The method of claim 2, further comprising reversing the transport of said particle to reintroduce said particle into a chamber through which it has already passed.

5. The method of claim 1, wherein said device comprises continuous tubing and surface tension valves separating said tubing into said plurality of chambers.

6. The method of claim 5, wherein said tubing comprises an inner surface coated by a polymer.

7. The method of claim 1, wherein said particle is a magnetic particle, a paramagnetic particle or a non-magnetic particle having a density of >1 or <1.

8. The method of claim 7, wherein transporting comprises passing a magnetic field along said tubing or subjecting said tubing to distinct intermittent magnetic fields to effect movement of said particle.

9. The method of claim 1, wherein transporting comprises applying centrifugal or gravitational force to said device such that said particle is transported through said plurality of chambers.

10. The method of claim 7, wherein said non-magnetic particle having a density of >1 is transported by density driven transport.

11. The method of claim 1, wherein introducing comprises injecting said sample through a wall of said first reaction chamber.

12. The method of claim 1, wherein introducing comprises movement of said sample into said first reaction chamber by capillary action.

13. The method of claim 1, wherein said particle is 0.1 to 10 micrometers in diameter.

14. The method of claim 1, wherein said tubing is 0.5 to $10^4$ micrometers in diameter.

15. The method of claim 1, wherein said non-reactive gas-based surface tension valve comprises a non-reactive gas having low vapor pressure and/or low surface tension.

16. A method of processing a sample comprising:
   (a) providing a device comprising continuous tubing forming a plurality of sequential chambers, each of said sequential chambers comprising a fluid and separated by a non-reactive gas-based surface tension valve that permits selective passage a particle between said sequential chambers;
   (b) introducing into said first chamber a particle comprising a surface reactant, the surface of which comprises analyte bound to said reactant;
   (c) transporting said particle from said first chamber into at least a second chamber through said non-reactive gas-based surface tension valve disposed therebetween; and
   (d) detecting the presence of said analyte.

17. The method of claim 16, further comprising mixing said particle with a sample to permit binding of said analyte to said reactant on said particle.

18. The method of claim 16, wherein said particle is a magnetic particle, a paramagnetic particle or a non-magnetic particle having a density of >1 or <1.

19. The method of claim 18, wherein transporting comprises passing a magnetic field along said tubing or subjecting said tubing to distinct intermittent magnetic fields to effect movement of said particle.

20. The method of claim 18, wherein said non-magnetic particle having a density of >1 is transported by density driven transport.

21. The method of claim 16, wherein transporting comprises applying centrifugal force to said device such that said particle is transported through said plurality of chambers.

22. The method of claim 16, wherein introducing comprises injecting said particles through a wall of said first chamber.

23. The method of claim 22, wherein introducing comprises movement of said sample into said first reaction chamber by capillary action.

24. The method of claim 16, wherein said device comprises at least three chambers.

25. The method of claim 24, wherein said device comprises said first reaction chamber, a first processing chamber and a first detection chamber, wherein said first processing chamber is disposed between said first reaction chamber and said first action chamber.

26. The method of claim 24, further comprising reversing the transport of said particle to reintroduce said particle into a chamber through which it has already passed.

27. The method of claim 16, wherein said non-reactive gas-based surface tension valve comprises a non-reactive gas having low vapor pressure and/or low surface tension.

28. The method of claim 15, wherein said non-reactive gas is air, carbon dioxide, nitrogen, argon, helium, or sulfur hexafluoride.

29. The method of claim 1, wherein said sample is a biological sample or an environmental sample.

30. The method of claim 29, wherein said biological sample is a tissue or fluid sample obtained from a patient.

31. The method of claim 29, wherein said environmental sample is a soil sample, a water sample, or a plant sample.

32. The method of claim 1, wherein said analyte is a protein, a polypeptide, a lipid, a carbohydrate, a nucleic acid, a heavy metal, an organochemical compound, a bacterium, a virus or a fungal cell.

33. The method of claim 27, wherein said non-reactive gas is air, carbon dioxide, nitrogen, argon, helium, or sulfur hexafluoride.

34. The method of claim 27, wherein said sample is a biological sample or an environmental sample.

35. The method of claim 34, wherein said biological sample is a tissue or fluid sample obtained from a patient.

36. The method of claim 34, wherein said environmental sample is a soil sample, a water sample, or a plant sample.

37. The method of claim 16, wherein said analyte is a protein, a polypeptide, a lipid, a carbohydrate, a nucleic acid, a heavy metal, an organochemical compound, a bacterium, a virus or a fungal cell.

* * * * *